(12) United States Patent
Regnier et al.

(10) Patent No.: US 10,974,056 B2
(45) Date of Patent: Apr. 13, 2021

(54) AUTONOMOUS CARDIAC IMPLANT OF THE LEADLESS CAPSULE TYPE, INCLUDING A PIEZOELECTRIC BEAM ENERGY HARVESTER

(71) Applicant: CAIRDAC, Antony (FR)

(72) Inventors: Willy Regnier, Longjumeau (FR); Alaa Makdissi, Paris (FR)

(73) Assignee: CAIRDAC, Antony (FR)

( * ) Notice: Subject to any disclaimer, the term of this patent is extended or adjusted under 35 U.S.C. 154(b) by 63 days.

(21) Appl. No.: 16/393,924

(22) Filed: Apr. 24, 2019

(65) Prior Publication Data

US 2019/0381325 A1 Dec. 19, 2019

(30) Foreign Application Priority Data

Jun. 14, 2018 (FR) ...................................... 1870691

(51) Int. Cl.
*A61N 1/37* (2006.01)
*A61N 1/378* (2006.01)
*A61N 1/375* (2006.01)
*H02N 2/18* (2006.01)
*H01L 41/113* (2006.01)

(52) U.S. Cl.
CPC ......... *A61N 1/3785* (2013.01); *A61N 1/3756* (2013.01); *A61N 1/37512* (2017.08); *A61N 1/37518* (2017.08); *H02N 2/181* (2013.01); *H02N 2/188* (2013.01); *H01L 41/1136* (2013.01)

(58) Field of Classification Search
CPC .............. A61N 1/3785; A61N 1/37512; A61N 1/37518; A61N 1/3756; H02N 2/181; H02N 2/188; H01L 41/1136
See application file for complete search history.

(56) References Cited

U.S. PATENT DOCUMENTS

| | | | |
|---|---|---|---|
| 3,943,936 A * | 3/1976 | Rasor | A61N 1/056 607/35 |
| 4,798,206 A | 1/1989 | Maddison et al. | |
| 2007/0149462 A1 | 6/2007 | Iyer et al. | |
| 2013/0238073 A1 | 9/2013 | Makdissi et al. | |
| 2015/0091415 A1 * | 4/2015 | Deterre | H01L 41/1136 310/339 |
| 2018/0185638 A1 | 7/2018 | Regnier | |

* cited by examiner

*Primary Examiner* — Amanda K Hulbert
*Assistant Examiner* — Natasha Patel
(74) *Attorney, Agent, or Firm* — Steven M. Greenberg, Esq.; Shutts & Bowen LLP

(57) ABSTRACT

The device includes an energy harvesting module with a pendular unit formed of an elastically deformable piezoelectric beam associated with an inertial mass. A multifunction part includes an axial through-recess with inner bearing surfaces opposite respective outer faces of the beam. These bearing surfaces having an increasing transverse spacing, such as, during an oscillation cycle, the beam comes into contact with one of the bearing surfaces, hence reducing the free length of the beam as the bending of the latter goes along. The multifunction part also allows rationalizing the manufacturing and the assembly of the capsule, with high-level integration of the inner components of the implant.

15 Claims, 5 Drawing Sheets

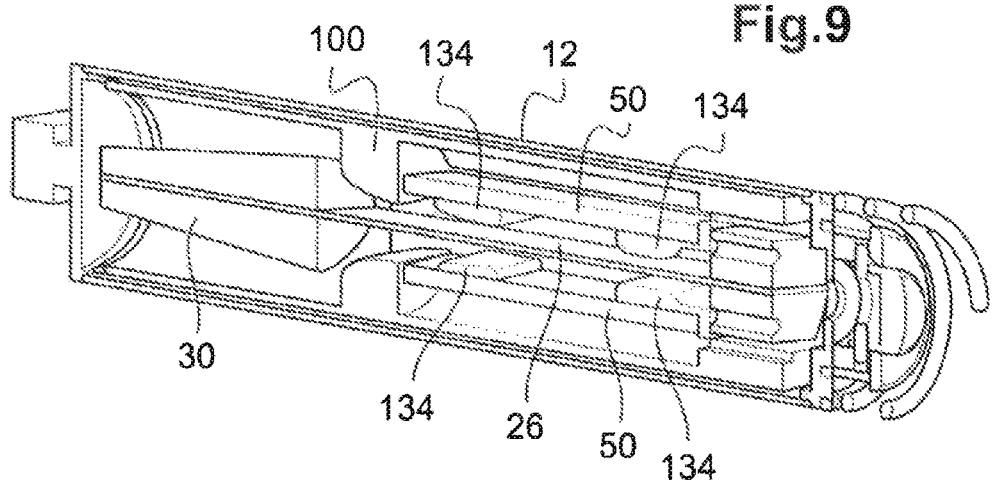
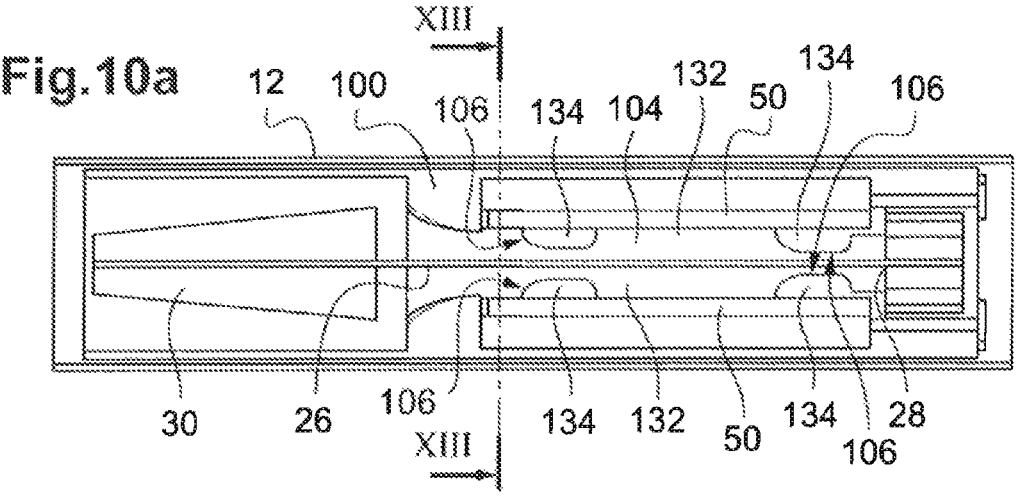
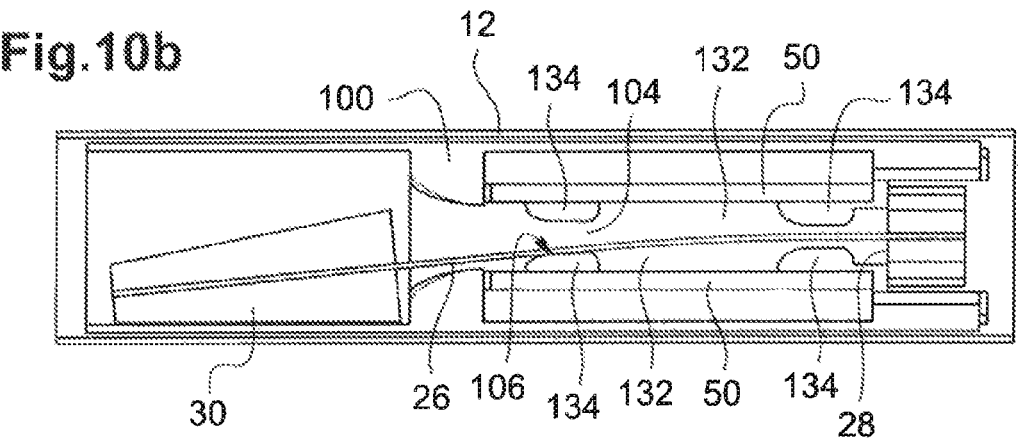

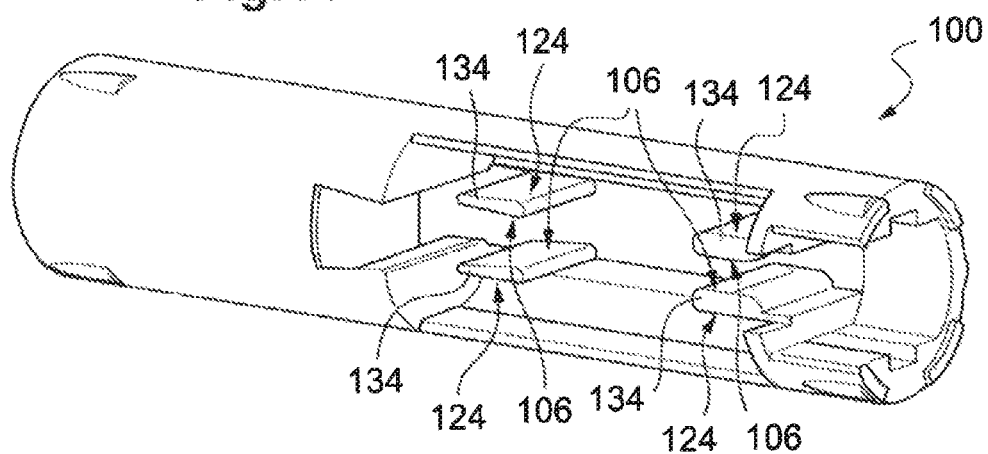
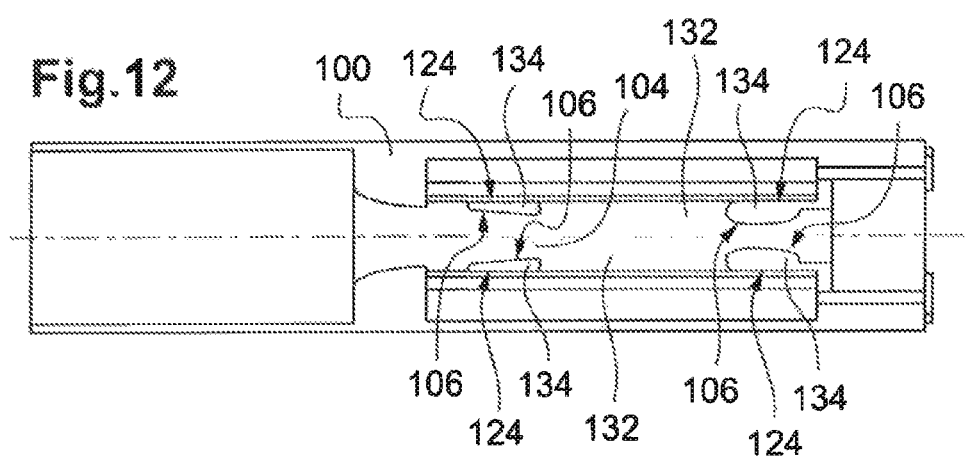
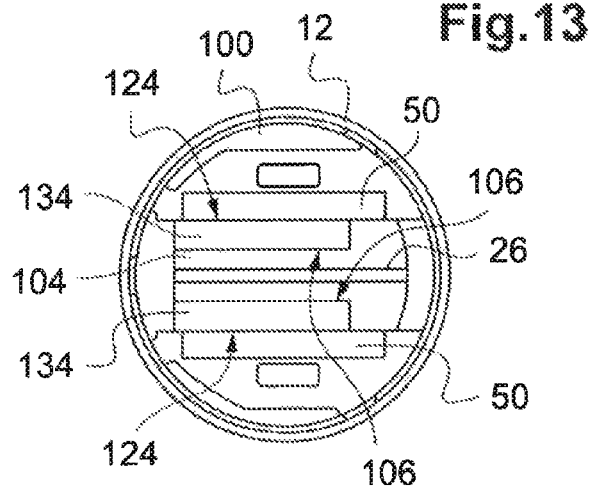

AUTONOMOUS CARDIAC IMPLANT OF THE LEADLESS CAPSULE TYPE, INCLUDING A PIEZOELECTRIC BEAM ENERGY HARVESTER

CROSS-REFERENCE TO RELATED APPLICATIONS

This application claims priority under 35 U.S.C. § 119(a) to French Patent Application Serial Number 1870691, filed Jun. 14, 2018, the entire teachings of which are incorporated herein by reference.

BACKGROUND OF THE INVENTION

Field of the Invention

The invention relates to implantable medical devices, in particular devices of the implantable autonomous capsule type and more particularly to leadless capsules or similar implantable devices whose energy harvester uses an inertial pendular unit subjected to the above-described external solicitations.

Description of the Related Art

Recent advances in miniaturization of active devices and advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

Indeed, one of the critical aspects of these miniaturized devices is the power autonomy. The life duration of such an implant being of about 8-10 years, taking into account the very small dimensions, it is not possible to use a conventional battery, even a high-density one.

The harvesting device, also known as "harvester" or "scavenger", addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, the vibrations of the cardiac tissues linked i.e. to closings and openings of cardiac valves, or blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and for charging the energy storage component. This powering system allows the device to operate in full power autonomy during its whole life.

This energy harvesting technique is particularly well adapted for powering the implanted autonomous capsules having no physical connection with a remote device. These capsules are called for this reason "leadless capsules", for distinguishing them from the electrodes or sensors arranged at the distal end of a lead, through the whole length of which run one or several conductors connected to a generator connected to the opposite, proximal end.

In the cardiac application case, the leadless capsule continuously monitors the rhythm of the patient and if necessary issues to the heart electrical pulses for stimulation, resynchronization and/or defibrillation in case of rhythm disorders detected by the capsule. The leadless capsule may be an epicardial leadless capsule, fixed to the outer wall of the heart, or an endocavitary capsule, fixed to the inner wall of a ventricular or atrial cavity, or a capsule fixed to the wall of a vessel near the myocardium. The fixation of the capsule to the implantation site is made through a protruding anchoring system extending the capsule body and designed to penetrate the cardiac tissue, in particular by means of a screw.

The capsule further includes various electronic circuits, sensors, etc., as well as wireless communication emitter/receiver means for the remote exchange of data, the whole being integrated in a body of very small size that can be implanted at sites whose access is difficult or that leave little space available, such as the apex of the ventricle, the inner wall of the atrium, etc. United States Patent Application Publication No. 2017/0151429 A1 by Regnier and United States Patent Application Publication No. 2009/0171408 A1 by Solem each describe various examples of such leadless intracardial capsules.

There exist several types of energy harvesters, based on different physical principles: system of the automatic wind-up watch movement type, mobile magnet system, bellows system or similar system collecting the blood pressure variations, etc.

An inertial pendular unit implements a transducer including in the capsule a mobile mass, called "seismic mass" or "inertial mass", which is driven according to the movements of the capsule, permanently subjected to the various external stresses described hereinabove. After each of these stresses, the inertial mass, which is coupled to an elastically deformable element, oscillates at a natural frequency of free oscillation.

The mechanical energy of the oscillation is converted into electrical energy by a mechanical-electrical transducer outputting an electrical signal. This signal is provided to a power management circuit of the implant, which rectifies and regulates the electrical signal to output a stabilized direct voltage or current, for powering the various electronic circuits and sensors of the implant, as well as for charging the energy storage component.

The mechanical-electrical transducer may be in particular a piezoelectric component cyclically and alternately stressed in bending so as to generate within its constituent material electrical charges that are collected at the surface of the component to be used by the self-powering system of the capsule. This piezoelectric component may in particular be a piezoelectric beam clamped at one end and coupled to the inertial mass at the other end, which is free. Such an energy harvester, for powering an implant from oscillations of a piezoelectric beam, is described in particular in U.S. Pat. No. 3,456,134 A to Ko.

It will be noted that the term "beam" has to be understood in its widest meaning, i.e. an elongated, thin and flat band, it being understood that the shape of this band is not necessarily rectangular not its thickness constant (as in the description of the particular embodiment that will be given hereinafter). The term "beam" hence covers elements that may have a width and/or a thickness that are not constant in the longitudinal direction, as well as, possibly, a deformability going beyond a single degree of freedom in bending.

BRIEF SUMMARY OF THE INVENTION

According to a first aspect, the present invention aims to propose a leadless capsule inner mechanical structure that, thanks to an original multifunction inner part, provides a high-level integration of the various elements of the capsule, and in particular the inertial pendular unit by implementing particularly compact, reliable and easy-to-industrialize means, without sacrificing the other requirements peculiar to an implantable leadless capsule, with in particular:

- construction as subassemblies which are separately assembled and controlled, then combined together at the time of the final mounting by simple and reliable assembly operations;
- centering and holding without clearance, in the tubular metal envelope of the leadless capsule, of a subassembly integrating the pendular unit and a maximum of mechanical and electrical elements of the implant;
- during the previous assembling of this subassembly, accurate centering and easy mounting of the pendular unit into a structure element that will then be supported in a tubular metal envelope of the leadless capsule;
- during the assembly of the pendular unit, centering and mounting the beam without transmission of parasitic stresses to the inertial beam-mass system;
- integration of the various electronic circuits of the leadless capsule without penalizing the available inner volume of the leadless capsule, in a manner fully compatible with the particular size and geometry of such a capsule (in particular an elongated tubular shape factor); and
- compatibility of assembly by implementation of usual industrial processes, such as laser welding, with, in this latter case, a heat transfer limited around the welding point.

According to a second aspect, the present invention aims at improving the energy harvesting of the mechanical-electrical transducer by an increased control of the oscillation regime of the inertial beam/mass pendular unit. Indeed, with the very small dimensions imposed to the leadless capsules, the electrical energy harvested at each oscillation is minimal, especially when the frequency and the amplitude of the heartbeats are low—the electrical powers rendered by a leadless capsule harvester being typically of the order of a few microwatts.

Actually, any technique making it possible, for a same level of mechanical stress on the capsule, to increase the produced quantity of electricity will allow powering the implant circuits and recharging the buffer battery, with an increased level of security.

In so far as it is not possible to increase the size of the pendular unit beam, nor the intensity of the mechanical stresses on the inertial mass, the invention proposes to improve the beam transduction efficiency by creating a bearing place against which the beam will bear during its bending movement, with for effect to introduce a contact point in a region of the beam that was initially a region of the free portion of the latter. This contact point, without preventing the beam to continue its bending up to its maximum amplitude, will dynamically modify the mechanical conditions of the bending and, consequently, the instantaneous level of mechanical-electrical transduction.

In particular, as will be seen in more details hereinafter, the additional stress created by the introduction and the displacement of a contact point during the bending of the beam modifies the length of the free portion of the beam, i.e. the cantilevered portion that is still able to bend; this free portion will then be shortened and this shortening will have for consequence to modify both the stress distribution within the beam (and hence the production of electricity by piezoelectric effect resulting from these stresses) and the vibratory regime of the beam/mass unit (the pendular oscillation frequency being directly function of the free length of the beam).

The objects exposed hereinabove are achieved, according to the present invention, by a device including an elongated tubular envelope provided with means for anchoring to a wall of a patient's organ, the tubular envelope receiving an electronic unit, an energy harvesting module and an energy storage component for powering the electronic unit.

In particular, the energy harvesting module includes:

- a pendular unit subjected to external stresses applied to the tubular envelope under the effect of movements of the wall and/or of blood flow rate variations in the surrounding medium, the pendular unit including a beam that is elastically deformable according to at least one degree of freedom, with a clamped end and an opposite, free end coupled to an inertial mass;
- a transducer adapted to convert into an oscillating electrical signal the mechanical energy produced by the oscillations of the pendular unit; and
- a power management circuit, adapted to rectify and regulate the oscillating electrical signal to output a stabilized direct voltage or current for powering the electronic unit and/or for charging the energy storage component.

Characteristically of the invention, the tubular envelope also receives a single-piece, central multifunction part made of a synthetic material, with at one of its ends a clamping region at which the beam is fastened to the multifunction part, and including an axial through-recess, into which the beam extends from the clamping region, over at least a part of its length.

According to various advantageous subsidiary characteristics:

- the multifunction part further includes, on the beam free end side, at least one stroke-limiting surface directed towards the inside, adapted to form a stop for the opposite inertial mass in a configuration of maximum bending of the beam;
- on the clamping region side, the axial through-recess of the multifunction part opens axially remote from the clamping point of the beam;
- the material of the multifunction part is a material of the group including the polyurethane thermoplastic polymers, the polyethylene terephthalate PET and the polyetheretherketone PEEK;
- the multifunction part is a part of tubular external shape, conjugated to the inner shape of the tubular envelope adapted to receive it;
- the multifunction part has, at its axial ends, centering shoulders formed at the periphery, in a continuous form or as discrete elements, in particular truncated shoulders adapted to allow a forced axial introduction of the multifunction part into the tubular envelope;
- in this latter case, it is advantageously provided that the maximum diameter of the multifunction part at the centering shoulders corresponds to the diameter of the inner surface of the tubular envelope, to within a negative clearance, making it possible to fasten the multifunction part with a tight fit in the tubular envelope after forced axial introduction into this latter;
- in particular, the material of the multifunction part may be a plastic material, and the material of the tubular envelope a metal material, whereby allowing an upsetting or a planing of the plastic material of the multifunction part during a forced introduction of the multifunction part into the tubular envelope;

in this latter case, the tubular envelope has advantageously, at one of its ends adapted to receive the multifunction part for its forced introduction, a bevelled edge adapted to plan or upset the plastic material of the multifunction part;

the multifunction part further includes, in the region of the clamped end of the beam, a cavity adapted to receive an added fitting forming the clamping part of the beam, advantageously in combination with faces and/or protrusions for aligning and/or centering the fitting in the cavity of the multifunction part.

According to another aspect of the invention, the axial recess includes inner bearing surfaces extending symmetrically opposite respective outer faces of the beam, the opposite inner bearing surfaces having between each other a variable transversal spacing, increasing in a direction going away from the clamping region; and the variable transversal spacing is such that i) the beam in the central position is not in contact with the bearing surfaces but ii) when, during an oscillation cycle of the pendular unit, the beam bends by moving away from its central position, the beam comes into contact with one of the inner bearing surfaces of the recess, hence reducing the free length of the beam as the bending of the latter goes along.

According to various advantageous subsidiary characteristics of this other aspect:

the inner bearing surfaces of the recess are surfaces having no discontinuity in the axial direction, defining in a radial plane a continuously variable curvature homologous to the curvature of the beam as its bending goes along, whereby progressively moving, in a direction going away from the clamping region, the point of contact of the beam against the inner bearing surface of the recess as the bending of the beam goes along;

the inner bearing surfaces of the recess may be ruled surfaces;

they may also be discontinuous surfaces in the axial direction, defining discrete bearing areas;

in this latter case, the transversal spacing between opposite discrete bearing areas corresponding to the spacing at this place between the beam and its central position, whereby moving, in a direction going away from the clamping region, the point of contact of the beam against the inner bearing surface of the recess when the beam comes into abutment against the corresponding discrete bearing area.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIGS. 9, 10a, 10b, 11, 12, 13 are homologous to FIGS. 4, 5a, 5b and 6 to 8, for an alternative embodiment of the multifunction part of the invention, in which the inner bearing surfaces against which the beam comes into abutment during its bending are no longer made as surfaces without discontinuities, but as discrete bearing areas.

DETAILED DESCRIPTION OF THE INVENTION

An exemplary embodiment of the device of the invention will now be described.

Figure 1:
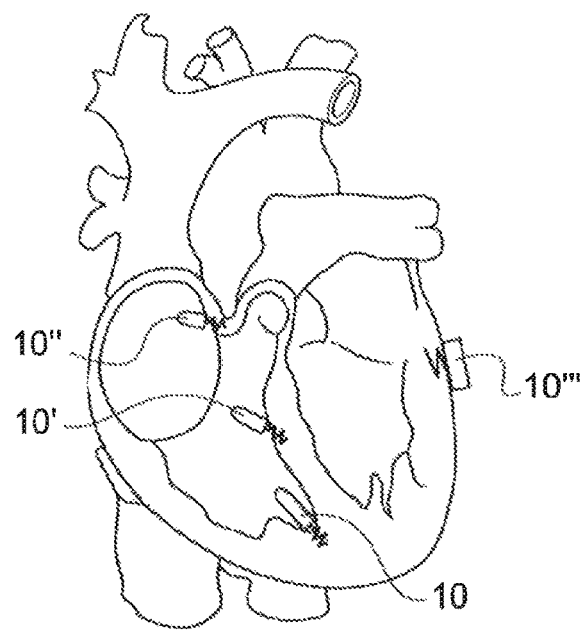
FIG. 1 illustrates medical devices of the leadless capsule type in their environment, with various examples of implantation sites in, on or near the heart of a patient.

In FIG. 1 are shown various possible sites for implanting a device of the leadless type, in a cardiac stimulation application. Hence, the capsule 10 is implanted inside a cavity of the myocardium (endocavitary implant), for example the apex of the right ventricle. As a variant, the capsule may also be implanted on the right interventricular septum, as in 10', or also on an atrial wall, as in 10". The device may also be an epicardial capsule placed on an external region of the myocardium, as in 10'''.

In each case, the leadless capsule is fixed to the cardiac wall using a protruding anchoring system entering the cardiac tissue for being held on the implantation site. Other anchoring systems may be used and modify in no way the implementation of the present invention.

Figure 2:
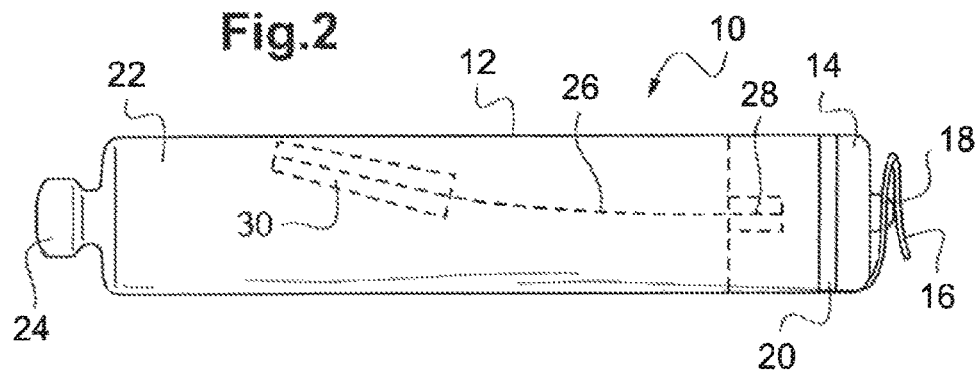
FIG. 2 is a general longitudinal view of a leadless capsule.

FIG. 2 is a general longitudinal view of a leadless capsule, including an energy harvester with a pendular unit.

The leadless capsule 10 is made in the external form of an implant with a body including an elongated cylindrical tubular envelope 12 enclosing the various electronic and power supply circuits of the capsule, as well as the pendular unit energy harvester. The typical dimensions of such a capsule are a diameter of the order of 6 mm for a length of about 25-40 mm.

The elongated tubular envelope 12 is closed at its front (proximal) end 14 by an element carrying an helical screw 16 for the anchoring of the capsule to a wall of a cardiac cavity, as illustrated hereinabove in relation to FIG. 1 (this anchoring mode being of course not limitative). A detection/stimulation electrode 18, in contact with the cardiac tissue at the implantation site, allows the collection of cardiac depolarization potentials and/or the application of stimulation pulses (in certain embodiments, the function of the electrode 18 is provided by the anchoring screw 16, which is then an active screw, electrically conductive and connected to the detection/stimulation circuit of the capsule). The electrode 18 in contact with the tissues is generally a cathode, and it is associated with an anode whose function is provided by a second, distinct electrode, most often an annular electrode, as in 20.

The opposite back (distal) end 22 of the leadless capsule 10 has an atraumatic rounded shape and is provided with suitable means 24 such as a gripping shape for the link to a guide-catheter or another implantation accessory usable at the implantation or the explantation of the capsule.

The leadless capsule 10 is provided with an energy harvesting module including an inertial pendular unit that, inside the capsule, oscillates following the various external stresses to which the leadless capsule is subjected, and that may in particular result from: the movements of the wall to which the capsule is anchored, which are transmitted to the implant by the anchoring screw 16; and/or the blood flow rate variations in the medium surrounding the implant, which produce oscillations of the implant at the rhythm of the heartbeats; and/or the various vibrations transmitted by the cardiac tissues.

The pendular unit may in particular be consisted by a piezoelectric beam 26 clamped in 28 at one of its ends and whose opposite, free end is coupled to a mobile inertial mass 30. The piezoelectric beam 26 is an elastically deformable flexible beam that constitutes, with the inertial mass 30, a pendular system of the mass-spring type, that, due to the inertia of the inertial mass 30, subjects the beam 26 to a deformation of the vibratory type on either side of a neutral or non-deformed position (hereinafter "central position"), corresponding to its stable rest position in the absence of any stress.

That way, this unit may be equated, as for its mechanical behaviour, to a structure of the "clamped/free beam" type, having a natural frequency of free oscillation, which is herein the frequency at which the mass-spring system oscillates. It will be noted that this natural oscillation frequency, typically of the order of a few tens of hertz, is notably higher than the frequency of the external cyclic stresses that correspond to the frequency of the heartbeats (at most a few hertz). Hence, at each heart contraction, the inertial mass (or other functionally similar mechanical member) will be stressed with a more or less high amplitude, then the inertial system will oscillate several times with decreasing amplitudes (bounces characteristic of a damped periodic oscillation), and will finally stabilize up to the following heartbeat, where the stress/oscillation cycle will be comparably repeated.

The piezoelectric beam 26 further performs a function of mechanical-electrical transducer making it possible to convert into electrical charges the mechanical stress that is applied to it when it bends, the charges being collected by electrodes formed at the surface of the beam to produce an electrical signal that, after rectification, stabilization and filtering will power the various electronic circuits of the capsule.

The beam is preferably a beam of the bimorphous type, i.e. capable of generating energy on its two faces when subjected to a deformation. Theses transduction properties are typical of a piezoelectric material, such as the PZT ceramics or the mono-crystals of the PMN-PT, barium titanate or lithium niobate type.

Figure 3:
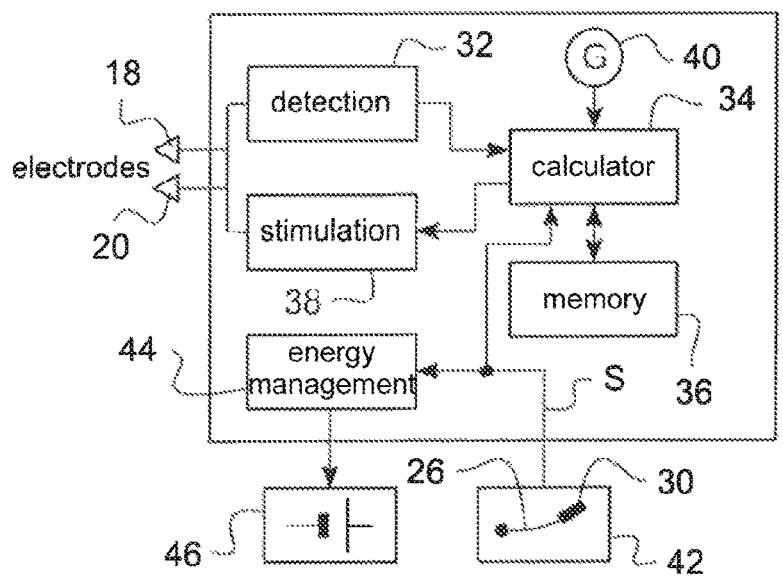
FIG. 3 shows, as a block diagram, the main internal constitutive elements of the leadless capsule.
Figure 4:
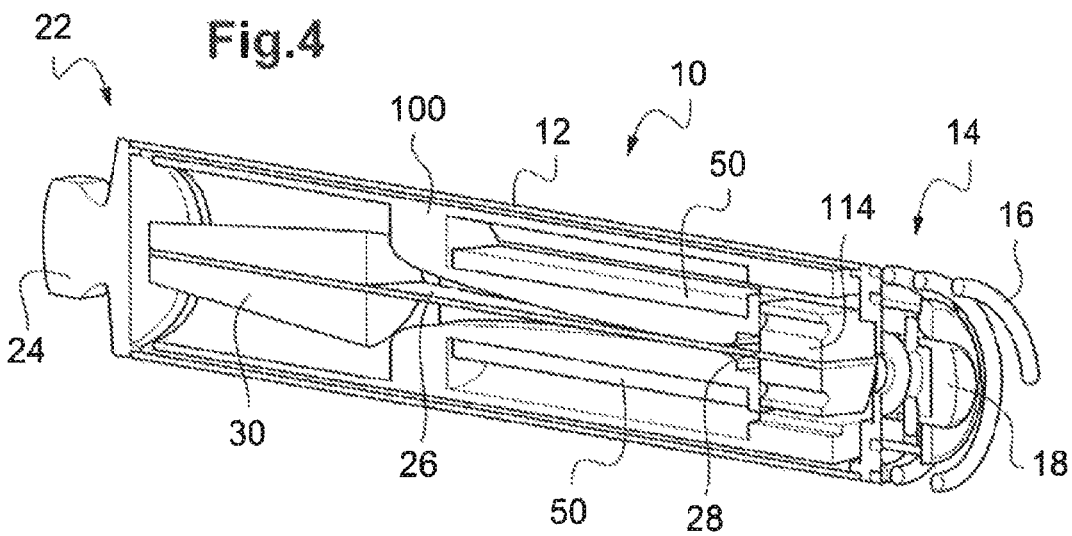
FIG. 4 is a longitudinal cross-sectional perspective view of the leadless capsule of FIG. 2, showing the mechanical configuration of the different elements located inside the tubular envelope of the capsule in an assembled configuration of the latter.

FIG. 3 is a synoptic of the various electric and electronic circuits integrated to the capsule, shown as functional blocks. These circuits are advantageously made as an ASIC or a combination of ASICs.

The block 32 represents a heart depolarization wave detection circuit, connected to the electrode 18 in contact with the cardiac tissue and to the opposite electrode 20. This detection block 32 includes filters and means for the analog and/or digital processing of the collected signal. The so-processed signal is applied to the input of the calculator 34 associated with a memory 36.

The electronic unit also includes a stimulation circuit 38 operating under the control of the calculator 34 to deliver myocardium stimulation pulses to the system of electrodes 18, 20 as needed.

The capsule may also include integrated sensors such that an accelerometer (G-sensor) 40 coupled to the calculator 34.

It is more over provided an energy harvesting circuit 42, consisted by the pendular unit formed by the piezoelectric beam 26 and the inertial mass 30 described hereinabove with reference to FIG. 2. As the piezoelectric beam 26 also performs a function of mechanical-electrical transducer, it converts into electrical charges the mechanical stresses undergone and produces a variable electrical signal S that is delivered to an energy management circuit 44. This circuit 44 rectifies and regulates the signal S so as to output a stabilized direct tension or current for powering the electronic unit and charging an integrated energy storage component 46, for example a rechargeable battery or a high-performance capacitor powering the electronic unit.

FIGS. 4 to 8 illustrate a first embodiment of the invention that will be described in detail, it being understood that the latter has no limitative character and that many variants may be contemplated without departing from the scope of the invention.

An inner multifunction part 100, characteristic of the invention, performs a number of functions allowing the operation of the energy harvesting system to be optimized in a reduced volume, while respecting the specific constraints of a long-term implantable stimulator, especially when it is a leadless capsule.

This central multifunction part 100, illustrated in isolation, in perspective view in FIG. 6 and in longitudinal cross-sectional view in FIG. 7, has a tubular external shape, with a cylindrical outer surface 102 conjugated to the inner shape of the cylindrical surface 48 of the tubular envelope 12 that receives this central multifunction part 100 (the way the latter is placed into the tubular body during the assembly of the capsule will be described hereinafter).

The multifunction part 100 includes in the centre thereof an axial recess 104 passing straight through it and inside which the beam 26 extends from the clamping region 28, over the major part of its length, between the clamping 28 and the inertial mass 30. This axial recess 104 has a flared shape widening progressively from the clamping 28 to the opening of the recess near the inertial mass 30.

In its oscillation movement under the effect of the external stresses received by the inertial mass, the beam is deformed in bending alternately in one direction and the other with respect to its central position (FIG. 5*a*), the two extreme positions of maximum bending (FIG. 5*b*) corresponding to a maximum amplitude.

Characteristically, the recess includes two opposite inner bearing surfaces 106, extending axially in the cantilevered, free region of the beam 26 and having between them a variable transverse spacing, increasing in the direction going from the clamping 28 to the inertial mass 30.

Indeed, the starting point of the invention lies in the observation that, for a piezoelectric beam, the maximal charge is produced where the stress is the higher, i.e. where the curvature of the bent beam is the greatest. Herein, for a clamped/free beam, this stress is maximum at the clamping, and decreases progressively and rapidly as the direction goes along towards the free end.

In other words, the maximum of the energy generated is at the clamping point, and the more the distance from this clamping increases, the less energy is generated. In other words, in the absence of a particular measurement, the beam length will have little effect on the mechanical-electrical conversion efficiency.

To improve this efficiency, the invention proposes to provide the inner bearing surfaces 106 with such a configuration that:

in the central position, the beam is not in contact with the bearing surfaces, but when, during an oscillation cycle of the pendular unit, the beam bends by moving away from its central position, the beam comes into contact with one of the inner bearing surfaces 106, hence reducing the free length of the beam as the bending of the latter goes along.

Figure 5A:
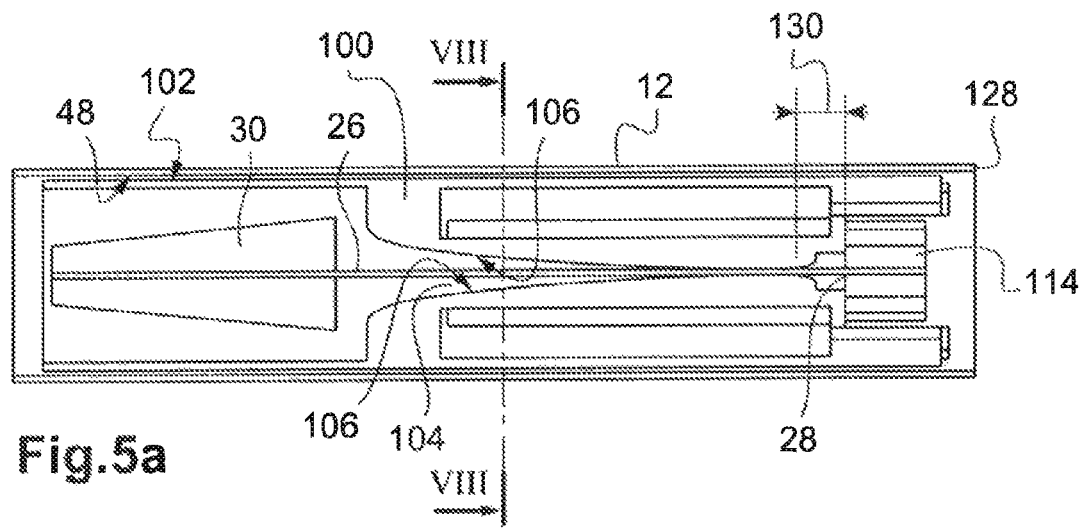
FIGS. 5a and 5b are lateral cross-sectional views of the central portion of the leadless capsule of FIGS. 2 and 4, showing in particular the configuration of the pendular unit inside the leadless capsule, in central position and in maximum bending, respectively.
Figure 5B:
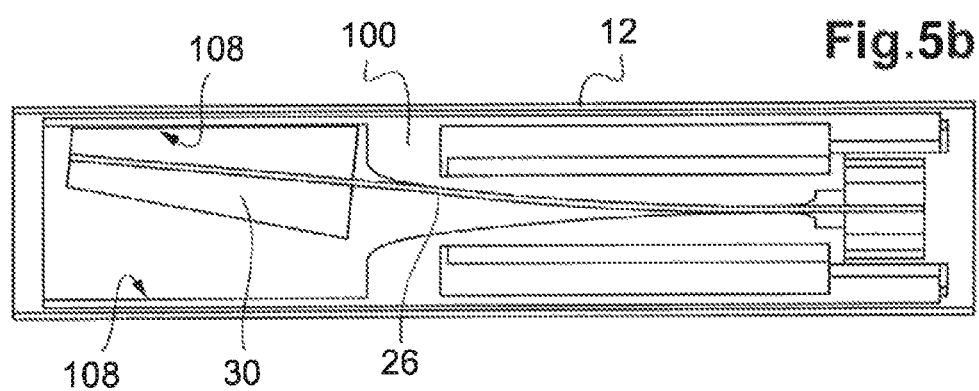
Figure 6:
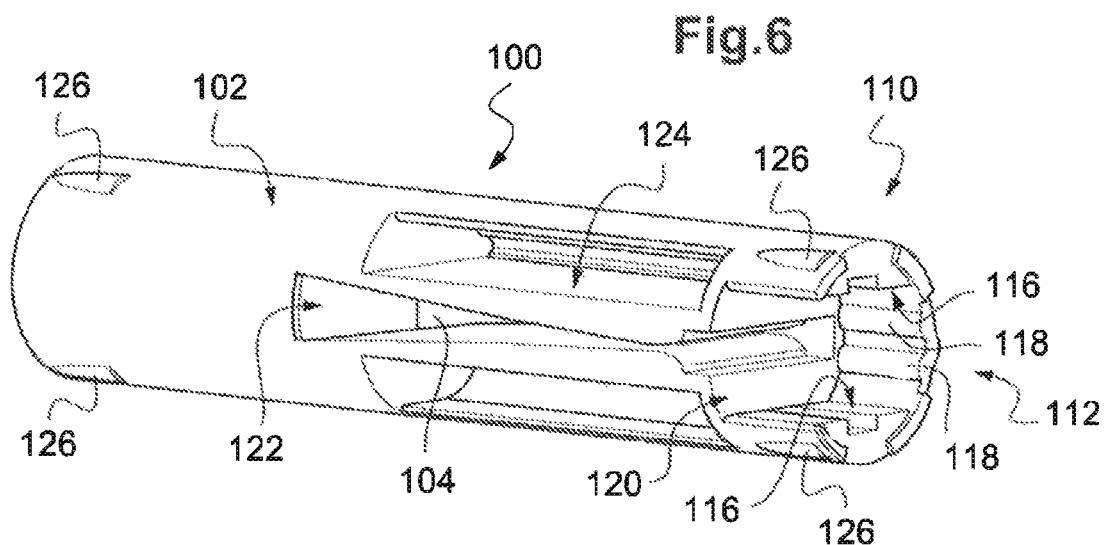
FIG. 6 is a perspective view of the multifunction part of FIGS. 4, 5a and 5b, shown in isolation, without the different elements supported or incorporated therein.
Figure 7:
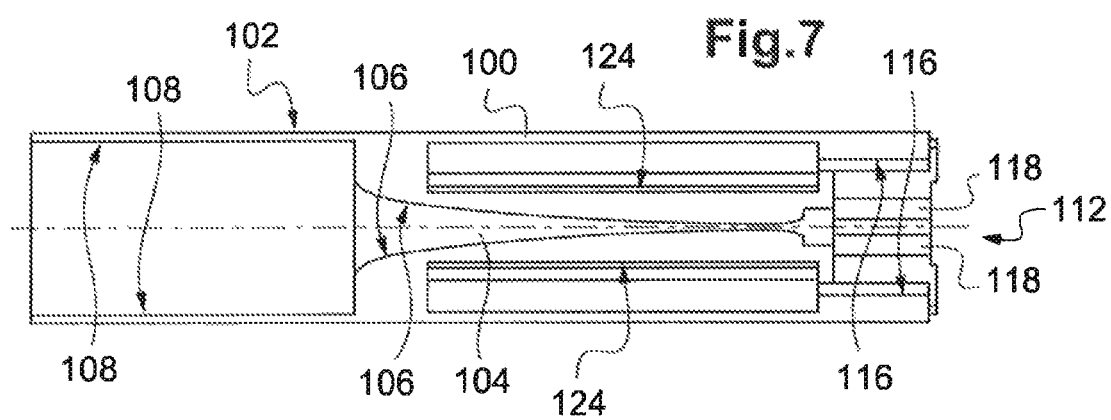
FIG. 7 is a longitudinal cross-sectional view, taken along a radial plane, of the multifunction part of FIG. 6.
Figure 8:
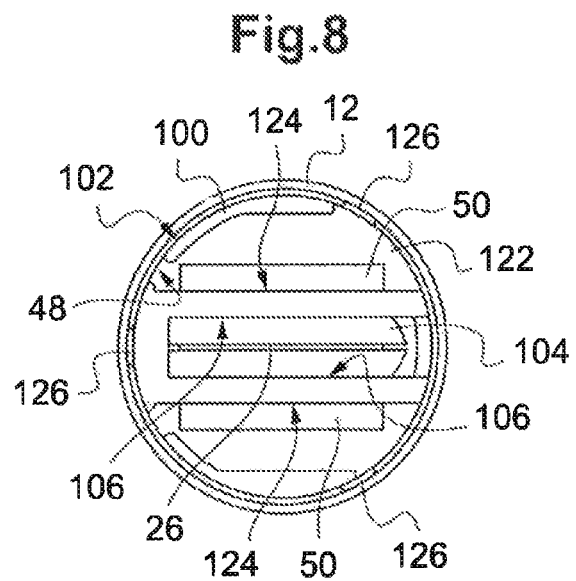
FIG. 8 is transverse cross-sectional view, taken along VIII-VIII of FIG. 5a, of the multifunction part of FIGS. 5a and 5b, with the different elements supported or incorporated therein.

In the embodiment illustrated in FIGS. 4 to 8, these inner bearing surfaces 106 are surfaces with no continuity solution in the axial direction, i.e. in a cross-sectional view (as in FIG. 7), they have a regular profile, with no discontinuity nor edge or protruding shape, and in the transverse direction (i.e. perpendicularly to the plane of the Figure in FIGS. 5 and 7), they have no curvature, in other words, these surfaces 106 are ruled surfaces as can be seen in the perspective view of FIG. 6 and in the radial cross-sectional view of FIG. 8.

The transverse spacing between the two opposite inner bearing surfaces 106 is such that the beam in the central position (configuration of FIG. 5a) in not in contact with these surfaces but that, in contrast, during an oscillation cycle when the beam bends by moving away from its central position, it touches the inner bearing surface 106 located opposite, as illustrated in FIG. 5b, in a configuration of maximum bending of the beam 26.

The variation law of the curvature of the inner bearing surfaces 106 in the axial direction is such that, during an oscillation cycle of the pendular unit, the beam comes progressively into contact with the bearing surface 106 towards which it bends, this contact hence reducing the free length of the beam as the bending of the latter goes along.

By making the contact between the beam and this bearing surface evolve during the bending, a dynamic interaction is produced between the beam 26 and the inner bearing surface 106. This allows controlling the bending of the beam and modifying dynamically the stiffness and natural vibration frequency thereof with, consequently, an increase of the instantaneous mechanical-electrical conversion efficiency.

More precisely, the fact to progressively seat the beam against the inner bearing surface 106 as the beam bends increases the stiffness of the latter (due to its shorter free length) and displaces axially the area of maximum stress towards the free end (towards the left in the Figure). This has for effect to increase the electric energy generated during an oscillation, because the maximum of electric energy collected is at the place where the bending stress of the piezoelectric beam is maximum.

Another advantage of the shortening of the bending beam during its oscillation is, in the frequency domain, a displacement towards higher natural oscillation frequencies, which results in an acceleration of the pendular unit movement with, here again, an increase of the mechanical-electrical conversion efficiency over the duration of an oscillation.

From the theoretical point of view, the dynamic curvature equation of the beam is that of a beam clamped on one side and free on the other side, which may be deduced from the Euler-Bernoulli theory. This theory describes an oscillation following several possible modes, but we will only consider herein the oscillation according to mode #1, which is the dominant mode where the beam is deformed following a profile having no point of inflexion, i.e. the concavity of the bent beam is, at any point of the beam, directed towards the same side as the central axis—herein, this concavity is always directed towards the side opposite to the central axis of the device.

The oscillation mode #1 (mode #1 of a clamped/free beam) is given by the following relationship:

$$\hat{w}_n = A_1 \left[ (\cosh\beta_n x - \cos\beta_n x) + \frac{\cos\beta_n L + \cosh\beta_n L}{\sin\beta_n L + \sinh\beta_n L}(\sin\beta_n x - \sinh\beta_n x) \right]$$

In this equation, x represents the position of one point on the beam and $\hat{w}_n$ represents the vertical displacement of the beam, x=0 corresponding to the clamping point (a 4th-order polynom gives a very good approximation of the displacement of the mode #1 because this mode is characterized by a very low value of □ and the Taylor series of order 4 constitutes a good approximation of sin, cos, sin h and cos h functions in the neighbourhood of zero).

For a progressive displacement of the point of contact between the beam and the opposite inner bearing surface 106, the profile in axial direction of the inner bearing surfaces 106 can be advantageously defined as being homologous to the curvature of the beam as its bending goes along, such curvature being described by the above relation deduced from the Euler-Bernoulli theory.

This definition is nevertheless not limitative, and other profile shapes may be contemplated to achieve the result consisting in creating and displacing a point of contact with the beam as the bending of the latter goes along.

On the distal side (on the left in the Figures), i.e. in the region of the inertial mass 30, the multifunction part 100 is in the form of a simple tubular wall whose inner surface 108 constitutes a stroke limitation surface for the inertial mass 30, the latter coming in abutment against the opposite inner surface 108 of the multifunction part 100 when the beam is in its maximum bending configuration (configuration of FIG. 5b).

The inertial mass has advantageously for that purpose a truncated shape; it is for example made from two separate elements, attached on either side of the beam 26 by bonding. The conical shape of the outer surface of the inertial mass allows optimizing the available space before the contact against the abutment surfaces 108, and hence the weight vs. size ratio.

On the side of the proximal end 110 (on the right in the Figures), i.e. on the side of the clamping region 28, the central multifunction part 100 includes a cavity 112 forming a housing for an added fitting 114 (FIGS. 4 and 5) forming the clamping part of the beam. At the time of assembly of the capsule, the beam/fitting assembly previously made in the form of a subassembly is introduced into the multifunction part 100, the alignment and the centering of the fitting 114 being advantageously made by faces 116 and/or protrusions 118 formed on the walls of the cavity 112.

To allow the introduction of the beam/fitting assembly into the multifunction part 100, the cavity 112 is open laterally at 120, as well as the axial recess 104, at 122, to allow an easy introduction and mounting of these two elements by a radial translation.

It is moreover provided a small free interval 130, for example of about 2 mm, between the opening of the axial recess 104 on the proximal side (i.e. on the side opposite to the clamping 28) and the clamping point itself of the beam, so as to avoid any stress application at this place when the beam is in the central position.

Moreover, the multifunction part 100 has advantageously support faces 124 intended to receive a printed circuit (PCB) 50, wherein this circuit can be easily inserted by the side, through an opening arranged in the multifunction part 100, leaving the support face 124 accessible.

Advantageously, it is provided support faces 124 arranged symmetrically, for the positioning of two PCBs 50. Actually, in order to optimize at best the space inside the capsule, the whole on-board electronics is made as electronic circuits mounted on PCBs arranged inside the capsule, in a region allowing the central space to be cleared for the beam 26. The two PCBs 50 are connected to each other, for example, by a flexible ribbon of conductors.

Finally, the multifunction part 100 includes at its outer surface centering shoulders 126 formed at the periphery of the distal part and of the proximal part, wherein these centering shoulders can be made in a continuous form, by a peripheral embossing, or as discrete elements, as illustrated in FIGS. 6 and 8.

These centering shoulders 126, which allow a positioning without clearance of the multifunction part 100 inside the tubular envelope 12 may in particular have a conical shape, with the apex of the cone directed towards the same side as all the shoulders, this side corresponding to a direction of introduction of the multifunction part 100 into the tubular envelope 12 at the time of assembly of these two elements.

The maximum diameter of the multifunction part 100 at the centering shoulders corresponds to the diameter of the inner surface 48 of the tubular envelope 12, to within a negative clearance allowing the fastening with interference fit of the multifunction part 110 in the tubular envelope 12 after forced axial introduction into the latter.

As regards the materials used, the material of the tubular envelope 12 is advantageously the titanium, but this may also be a stainless steel, for example 316L steel, or a metal such as tantalum or a nickel-titanium alloy of the nitinol type. The thickness of the tubular envelope is typically of the order of 0.15-0.25 mm.

The material used for the inertial mass is advantageously tungsten, which has a high density for a controlled production cost.

As regards the multifunction part 100, this part is advantageously made of a dielectric material such as a polyurethane thermoplastic polymer such as Tecothane® or a polymer such as polyethylene terephthalate PET and polyetheretherketone PEEK, or another injectable plastic material.

The part is advantageously made single-piece by injection moulding of the plastic material.

But other techniques may be implemented as a variant for manufacturing this single-piece multifunction part, in particular 3D-printing from a dielectric polymer resin.

The use for the multifunction part 100 of a synthetic material as indicated hereinabove allows in particular, during the assembly into the metal tubular envelope 12, the introduction of the plastic part by an axial thrust, the two parts being positioned by a cone/circle contact. The thin thickness of the metal tubular envelope further makes it possible to easily form at the end thereof a bevelled edge 128 (FIG. 5a), which will serve to plane or to upset the synthetic material of the multifunction part 100 during the insertion of the latter, the bevelled edge acting as a die-cut; the material in excess will remain caught between the tube 12 and the multifunction part 100 on the back of the cones of the shoulders 126. The final locking may possibly be made by addition of glue to immobilize these two parts.

To sum-up, the operations of the assembly process in which the multifunction part 100 intervene are the following:

positioning the two PCBs 50 on the corresponding support surfaces 124, on either side of the multifunction part 100;

electrically connecting the PCBs (it will be noted that the configuration of the multifunction part 100 makes these PCBs accessible by the side, the required welding being easy to make by an operator under a binocular device);

laterally inserting the beam/fitting assembly through the lateral openings 120, 122, then bonding the fitting in place in the cavity 112;

positioning the inertial mass 30 at the free end of the beam 26;

inserting into the metal envelope 12 the multifunction part 100 equipped with the interconnected PCBs and the beam/inertial mass pendular unit, by axial translation with self-centering and fastening with interference fit thanks to the shoulders 126;

definitely immobilizing the multifunction part 100 in the tubular envelope 12 by bonding;

adding the distal and proximal elements 14 and 22 on the tubular envelope 12, by per se known techniques, such as those described in particular in EP 2 959 940 A1 (Sorin CRM).

FIGS. 9 to 13 are homologous to FIGS. 4 to 8 described in detail hereinabove, for another embodiment, wherein, all things being otherwise identical, the central multifunction part 100 is axially pierced in the centre thereof, in the region of the support surfaces 124 of the PCBS.

More precisely, due to these recesses 132, the wall between the inner bearing surfaces 106 and the support surfaces 124 of the PCBs is no longer a continuous wall, as in the previous embodiment, but is reduced to one or several transverse pairs 134 extending on either side of the axial through-recess 104.

Consequently, the bearing surfaces 106 are no longer surfaces that are continuous in axial direction, but are discrete bearing areas, two in number in the illustrated example.

As in the previous case, the axial spacing between opposite discrete bearing areas is homologous to the spacing existing at this place between the beam, when it is bent, and the central position thereof. Hence, when the beam is in a maximum bending configuration (as illustrated in FIG. 10b), the outer face of the beam comes into contact with the corresponding inner bearing surface 106 of the most distal cross-piece 134 (i.e. that which is closest to the inertial mass 30).

As in the previous case, this mechanism allows displacing, in a direction going away from the clamping 28, the point of contact of the beam 26 against the inner bearing surface of the recess 104 when the beam comes into abutment against the corresponding discrete bearing area 106.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. An active medical device of the implantable autonomous capsule type, comprising an elongated tubular envelope provided with means for anchoring to a wall of a patient's organ, the tubular envelope receiving an electronic unit, an energy harvesting module and an energy storage component for powering the electronic unit, wherein the energy harvesting module comprises:
    a pendular unit subjected to external stresses applied to the tubular envelope under the effect of movements of said wall and/or of blood flow rate variations in the surrounding medium, the pendular unit comprising a beam that is elastically deformable according to at least one degree of freedom, with a clamped end and an opposite, free end coupled to an inertial mass; a transducer adapted to convert into an oscillating electrical signal the mechanical energy produced by the oscillations of the pendular unit; and
    a power management circuit, adapted to rectify and regulate the oscillating electrical signal to output a stabilized direct voltage or current for powering the electronic unit and/or for charging the energy storage component, and wherein the tubular envelope also receives a single-piece, central multifunction part made of a synthetic material, with at one of its ends a clamping region at which the beam is fastened to the multifunction part, and comprising an axial through-recess, into which the beam extends from the clamping region, over at least a part of its length,
    the axial-recess comprising inner bearing surfaces extending symmetrically opposite respective outer faces of the beam, the opposite inner bearing surfaces having between each other a variable transversal spacing, increasing in a direction going away from the clamping region; and said variable transversal spacing is such that i) the beam in the central position is not in contact with the bearing surfaces but ii) when, during an oscillation cycle of the pendular unit, the beam bends by moving away from its central position, the beam comes into contact with one of the inner bearing surfaces of the recess, hence reducing the free length of the beam as the bending of the latter goes along.

2. The device of claim 1, wherein the multifunction part further comprises, on the beam free end side, at least one stroke-limiting surface directed towards the inside, adapted to form a stop for the opposite inertial mass in a configuration of maximum bending of the beam.

3. The device of claim 1, wherein, on the side of the clamping region, the axial through-recess of the multifunction part opens axially remote from the clamping point of the beam.

4. The device of claim 1, wherein the material of the multifunction part is a material of the group comprising the polyurethane thermoplastic polymers, the polyethylene terephthalate PET and the polyetheretherketone PEEK.

5. The device of claim 1, wherein the multifunction part is a part of tubular external shape, conjugated to the inner shape of the tubular envelope adapted to receive it.

6. The device of claim 5, wherein the multifunction part has, at its axial ends, centering shoulders formed at the periphery, in a continuous form or as discrete elements.

7. The device of claim 6, wherein the centering shoulders are truncated shoulders adapted to allow a forced axial introduction of the multifunction part into the tubular envelope.

8. The device of claim 6, wherein the maximum diameter of the multifunction part at the centering shoulders corresponds to the diameter of the inner surface of the tubular envelope, to within a negative clearance, making it possible to fasten the multifunction part with a tight fit in the tubular envelope after forced axial introduction into the tubular envelope.

9. The device of claim 8, wherein the material of the multifunction part may be a plastic material, and the material of the tubular envelope is a metal material, whereby allowing an upsetting or a planing of the plastic material of the multifunction part during a forced introduction of the multifunction part into the tubular envelope.

10. The device of claim 9, wherein the tubular envelope has, at one of its ends adapted to receive the multifunction part for its forced introduction, a bevelled edge adapted to plan or upset the plastic material of the multifunction part.

11. The device of claim 1, wherein the multifunction part further comprises, in the region of the clamped end of the beam, a cavity adapted to receive an added fitting forming the clamping part of the beam.

12. The device of claim 11, wherein the multifunction part further comprises faces and/or protrusions for aligning and/or centering the fitting in the cavity of the multifunction part.

13. The device of claim 1, wherein the inner bearing surfaces of the recess are surfaces having no discontinuity in the axial direction, defining in a radial plane a continuously variable curvature homologous to the curvature of the beam as its bending goes along, whereby progressively moving, in a direction going away from the clamping region, the point of contact of the beam against the inner bearing surface of the recess as the bending of the beam goes along.

14. The device of claim 1, wherein the inner bearing surfaces of the recess are ruled surfaces.

15. The device of claim 1, wherein the inner bearing surfaces of the recess are discontinuous surfaces in the axial direction, defining discrete bearing areas, the transversal spacing between opposite discrete bearing areas corresponding to the spacing at this place between the beam and its central position, whereby moving, in a direction going away from the clamping region, the point of contact of the beam against the inner bearing surface of the recess when the beam comes into abutment against the corresponding discrete bearing area.

\* \* \* \* \*